(12) United States Patent
Wheaton et al.

(10) Patent No.: US 8,126,230 B2
(45) Date of Patent: Feb. 28, 2012

(54) METHOD OF MOTION CORRECTION FOR DYNAMIC VOLUME ALIGNMENT WITHOUT TIMING RESTRICTIONS

(75) Inventors: Andrew J. Wheaton, Shaker Heights, OH (US); Deepak V. Bhat, Solon, OH (US); Michael R. Thompson, Cleveland Heights, OH (US); Wayne R. Dannels, Mentor, OH (US); Ad L. Moerland, Rilland (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 764 days.

(21) Appl. No.: 12/296,939

(22) PCT Filed: Apr. 3, 2007

(86) PCT No.: PCT/US2007/065838
§ 371 (c)(1),
(2), (4) Date: Oct. 13, 2008

(87) PCT Pub. No.: WO2007/124243
PCT Pub. Date: Nov. 1, 2007

(65) Prior Publication Data
US 2009/0116761 A1    May 7, 2009

Related U.S. Application Data

(60) Provisional application No. 60/745,255, filed on Apr. 20, 2006.

(51) Int. Cl.
*G06K 9/00* (2006.01)
(52) U.S. Cl. .................. 382/128; 382/131; 382/254
(58) Field of Classification Search .................. None
See application file for complete search history.

(56) References Cited

U.S. PATENT DOCUMENTS

| 5,323,110 A | 6/1994 | Fielden et al. |
|---|---|---|
| 6,559,641 B2 | 5/2003 | Thesen |
| 2003/0153826 A1 | 8/2003 | Jack et al. |
| 2004/0136490 A1 * | 7/2004 | Edic et al. .................. 378/4 |

(Continued)

FOREIGN PATENT DOCUMENTS
EP    1249710 A2    10/2002

OTHER PUBLICATIONS

Gedat, E., et al.; Prospective Registration of Human Head Magnetic Resonance Images for Reproducible Slice Positioning Using Localizer Images; 2004; J. of Magnetic Resonance Imaging; 20:581-587.

(Continued)

*Primary Examiner* — Minh N Tang

(57) ABSTRACT

When performing repetitive scans of a patient using a magnetic resonance imaging machine or the like, patients often tend to move as they relax during a lengthy scanning session, causing movement in the volume or portion of the patient being scanned. A prospective motion correction component accounts for patient movement by calculating transformation data representative of patient movement in multiple planes, as well as rotational movement, and a host evaluates the change in position relative to a most recent scanning geometry of the patient or dynamic volume. In this manner, correction or adjustment to the scanning geometry employed by an associated scanner is made only for the differential between the current geometry and the most recent geometry, to mitigate redundant adjustment that can result in oscillatory over—and under—compensation during adjustments.

22 Claims, 10 Drawing Sheets

U.S. PATENT DOCUMENTS

2006/0133564 A1* 6/2006 Langan et al. .................... 378/8

OTHER PUBLICATIONS

Manke, D., et al.; Model Evaluation and Calibration for Prospective Respiratory Motion Correction in Coronary MR Angiography Based on 3-D Image Registration; 2002; IEEE Transactions on Medical Imaging; 21(9)1132-1141.

Mathiak, K., et al.; Evaluation of Motion and Realignment for Functional Magnetic Resonance Imaging in Real Time; 2001; Magnetic Resonance in Medicine; 45:167-171.

Thesen, S., et al.; Prospective Acquisition Correction for Head Motion with Image-Based Tracking for Real-Time fMRI; 2000; Magnetic Resonance in Medicine; 44:457-465.

* cited by examiner

METHOD OF MOTION CORRECTION FOR DYNAMIC VOLUME ALIGNMENT WITHOUT TIMING RESTRICTIONS

CROSS REFERENCE TO RELATED APPLICATIONS

This application claims the benefit of U.S. provisional application Ser. No. 60/745,255 filed Apr. 20, 2006, which is incorporated herein by reference.

The present application finds particular application in error correction in medical scanning systems or the like. However, it will be appreciated that the described technique(s) may also find application in other types of scanning systems and/or other error correction systems.

Retrospective motion correction as part of post-processing uses volume registration with pixel interpolation. Retrospective correction is used to correct for in-plane transformations (e.g., x,y translations) which require simple shifts and rotations of image pixels. But, retrospective correction is weak when correcting through-plane motion (e.g., translation in the slice or axial direction) which necessitates interpolation between slices thereby introducing significant partial voluming effects and revolution degradation. The image information lost to through-plane motion would be unable to be entirely recaptured by retrospective correction using interpolation.

A version of prospective motion correction, known as prospective acquisition correction has been previously implemented, but the processes of image reconstruction, volume registration, geometry calculation, and data transfer must be completed in the remaining time between the end of the acquisition of the last dynamic scan and the beginning of the next one. In a system with a dedicated reconstruction processor and modern workstation, the total duration of these processes can be on the order of seconds. Thus, in such conventional systems, repetition time (TR) must be sufficiently long to permit for completion of the requisite calculations. If TR is too short and the scanner does not receive geometry updates before the next acquisition is initiated, an undesirable oscillatory pattern arises, comprising periods of overcompensation that alternate with periods of under-compensation.

Thus, there is an unmet need in the art for systems and methods that facilitate providing real-time, on-the-fly motion correction that is independent of repetition time constraints in order to improve scan quality and reduce overall scan time.

In accordance with one aspect, a system for prospective motion correction (PMC) includes a scanner that scans a dynamic volume in a patient, and a reconstructor that reconstructs measurement data received from the scanner into image data. The system further includes a PMC component that analyzes the image data and generates geometry transformation data related to a change between a most recent geometry associated with an orientation and position of the dynamic volume and a new geometry associated with the orientation and position of the dynamic volume, and a host that generates geometry updates for the scanner between successive scans as a function of the geometry transformation data.

In accordance with another aspect, a method of performing prospective motion correction during a patient scan includes providing an original geometry to a scanner (10), scanning the dynamic volume, and generating image data indexed to an original geometry. The method further includes executing a PMC protocol that calculates transformation information from the image data, calculating patient motion as a function of the transformation information and the original geometry, and determining a new geometry as a function of the patient motion. Still further, the method includes providing the new geometry to the scanner (10) for a subsequent scan, and repeating the scanning, generating, executing, calculating, determining and providing steps using the new geometry.

One advantage is that the prospective motion correction (PMC) algorithm is not constrained by scanning repetition time limits.

Another advantage resides in bookkeeping mechanisms that ensure that patient motion is not redundantly addressed, mitigating an undesirable oscillatory correction pattern.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
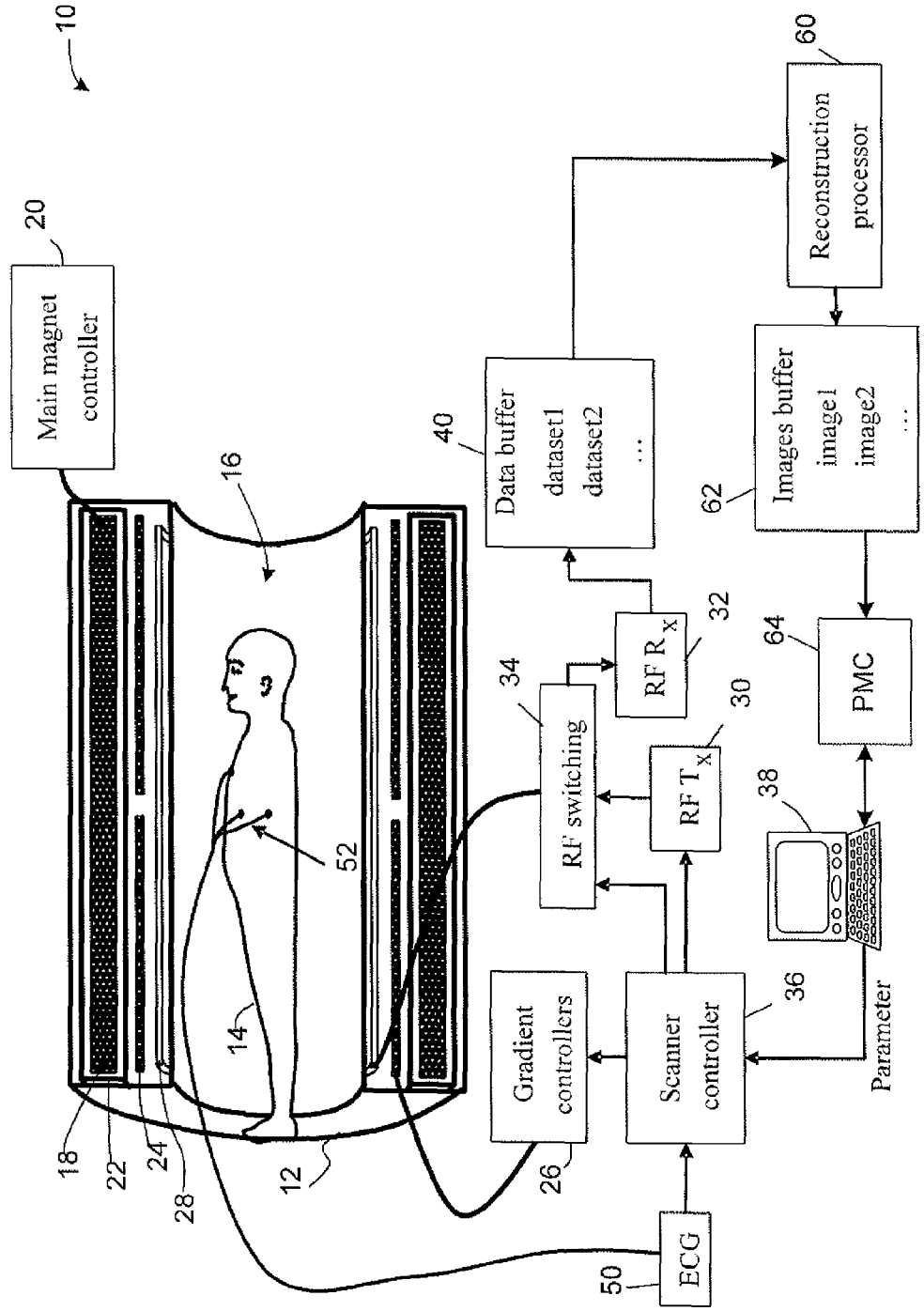
FIG. 1 illustrates a magnetic resonance scanning system for performing prospective motion correction (PMC) using a scanner device, in accordance with various embodiments described herein.

FIG. 1 illustrates a magnetic resonance scanning system 10 for performing prospective motion correction (PMC) using a scanner device 12, in accordance with various embodiments described herein. PMC techniques measure changes in geometry due to subject motion during the acquisition of a dynamic series (e.g., during a scan). Subject motion is corrected in real time on the scanner, resulting in an improvement in volume alignment in an image series. The subject innovation thus represents an improvement on previous motion correction techniques. For instance, conventional schemes required all processing to be performed prior to the beginning of a next acquisition, thus limiting usefulness to long repetition-time (TR) scans. Scanner 10 includes features which allow the scanner to be continually updated on-the-fly as corrections are made. Thus, PMC is not hindered by pulse sequence timing restrictions, thereby offering an advantage over previous motion correction schemes. In this manner, real-time adjustments can be made to scanning geometries as a patient moves during a relatively long scan (e.g., 10 minutes, 30 minutes, etc.). The following paragraphs provide insight into the operation and structure of the scanner with which a PMC algorithm is employed.

The scanner 10 includes a scanner housing 12 in which a patient 14 or other subject is at least partially disposed with a heart, brain, or other organ or anatomical region to be studied, positioned in a scanning region 16 of the scanner 10. Although described with reference to a bore-type scanner, it is to be appreciated that the scanner could also be an open-magnet scanner or other type of magnetic resonance scanner. A main magnet 18 disposed in the scanner housing 12 is controlled by a main magnet controller 20 to generate a static ($B_0$) magnetic field in at least the scanning region 16. Typically, the main magnet 18 is a persistent superconducting magnet surrounded by cryoshrouding 22, although a resistive magnet can also be used. In some embodiments, the main magnet 18 generates a main magnetic field of between about 0.23 Tesla and about 7 Tesla; however, main magnetic fields of strengths above or below this typical range are also contemplated. A gradient system including magnetic field gradient coils 24 arranged in or on the housing 12 and corresponding gradient controllers 26 superimpose selected magnetic field gradients on the main magnetic field in at least the scanning region 16. Typically, the magnetic field gradient coils 24 include coils for producing three orthogonal magnetic field gradients, such as x-, y-, and z-gradients.

A generally cylindrical whole-body coil 28 is mounted substantially coaxially with the bore of the magnetic resonance scanner 10. The whole-body coil 28 may be, for example, a quadrature birdcage coil, transverse electromagnetic (TEM) coil, or so forth. Additionally or alternatively, one or more local radio frequency coils such as a surface coil or plurality of surface coils, a SENSE coil array, a torso coil, or so forth (not shown) can be employed. In the embodiment of FIG. 1, the whole-body coil 28 performs both transmit and receive functions. That is, the whole-body coil 28 is energized at a magnetic resonance frequency by one or more radio frequency transmitters 30 to excite magnetic resonance in the subject 14, and the whole-body coil 28 is also used in conjunction with one or more radio frequency receivers 32 to receive magnetic resonance signals emanating from the subject 14 responsive to such excitation. Suitable radio frequency switching circuitry 34 are provided to enable the whole-body coil 28 to perform both transmit and receive functions.

While shown as a separate unit, in some embodiments the radio frequency switching circuitry or portions thereof may be integrated into the whole-body coil, the radio frequency transmitter, or the radio frequency receiver. In other contemplated embodiments, the whole-body coil 28 performs the transmit function, while one or more local radio frequency coils receives the generated magnetic resonance signals. In other contemplated embodiments, the whole-body coil 28 is omitted and one or more local radio frequency coils perform both transmit and receive functions. It is still further contemplated to use the whole-body coil 28 as a receive coil while magnetic resonance is excited using one or more local radio frequency coils.

The magnetic resonance scanner 10 operates under the control of a scanner controller 36. A user interface 38 enables a radiologist or other user to select one or more magnetic resonance sequences, and also enables the user to set or modify parameters of the sequence. The scanner 10 operates under the control of the scanner controller 36 in accordance with the selected sequence to excite magnetic resonance and generate magnetic resonance data that are stored in a data memory or buffer 40. The sequence can be re-executed to generate multiple sets of data, such as the illustrated dataset1, dataset2, . . . shown in the data buffer 40 corresponding to re-executing the selected sequence with different values for the set or modified parameter. Optionally, patient monitor 50 with leads 52, or additional monitor or other auxiliary equipment, monitors the patient 14 during the magnetic resonance data acquisition. For example, if the monitor is an ECG device, the monitor can provide cardiac gating information to ensure that data is acquired at about a selected cardiac phase such as at about the diastolic phase or about the systolic phase. In some embodiments, the generation of saturation recovery or inversion recovery data is cardiac gated using the monitor 50 such that data are acquired in multiple cardiac phases, and multiple saturation recovery or inversion recovery data sets are derived, in which each data set is assigned to a selected cardiac phase.

A reconstruction processor 60 reconstructs the acquired magnetic resonance data, or portions thereof, into a reconstructed image. In the illustrated embodiment, each re-execution of the sequence generates a separate informational magnetic resonance dataset, such as the example dataset1 and dataset2 recovery datasets acquired with the parameter set at different values, respectively, for successive executions of the sequence. These datasets are each reconstructed into a reconstructed image by the reconstruction processor 60, for example to generate reconstructed images of the respective datasets, and so forth, which are suitably stored in an images memory or buffer 62. According to an example, recovery data may be included in the processing after correction of motion-induced displacement or deformation, or image artifacts resulting from patient motion occurring during data acquisition.

A PMC component 64 analyzes image data using one or more prospective motion correction algorithms to compensate for patient movement during a scan. According to one embodiment, the PMC component dynamically updates patient position information as a function of change in position while accounting for redundant data that can cause oscillatory patterns of over-compensation and under-compensation. For instance, the PMC receives dynamic images from the reconstruction processor 60 and/or the image buffer 62, and recognizes that multiple images indexed to the same geometry will produce substantially identical transformation data (e.g., data describing 3-D position change, rotational position change, etc.). For example, by comparing subsequent images, a transform that describes the translational shift and, optionally, rotation of characteristic prints of the two images is readily determined. This transform is then applied to the scan controller 36 to adjust the RF frequencies of the gradient magnetic fields applied by the RF coil 28 and the gradient coils 24 to keep the imaging volume and the image slices or planes aligned consistently with the selected portion of the patient anatomy. The PMC component ensures that the first transformation registered patient motion, resulting in a change to a most recent geometry used by the scanner. However, the PMC component additionally ensures that the subsequent transformations, and associated redundant data, do not register any change to patient motion, thus protecting the system scanner from entering an oscillatory compensation pattern.

Figure 2:
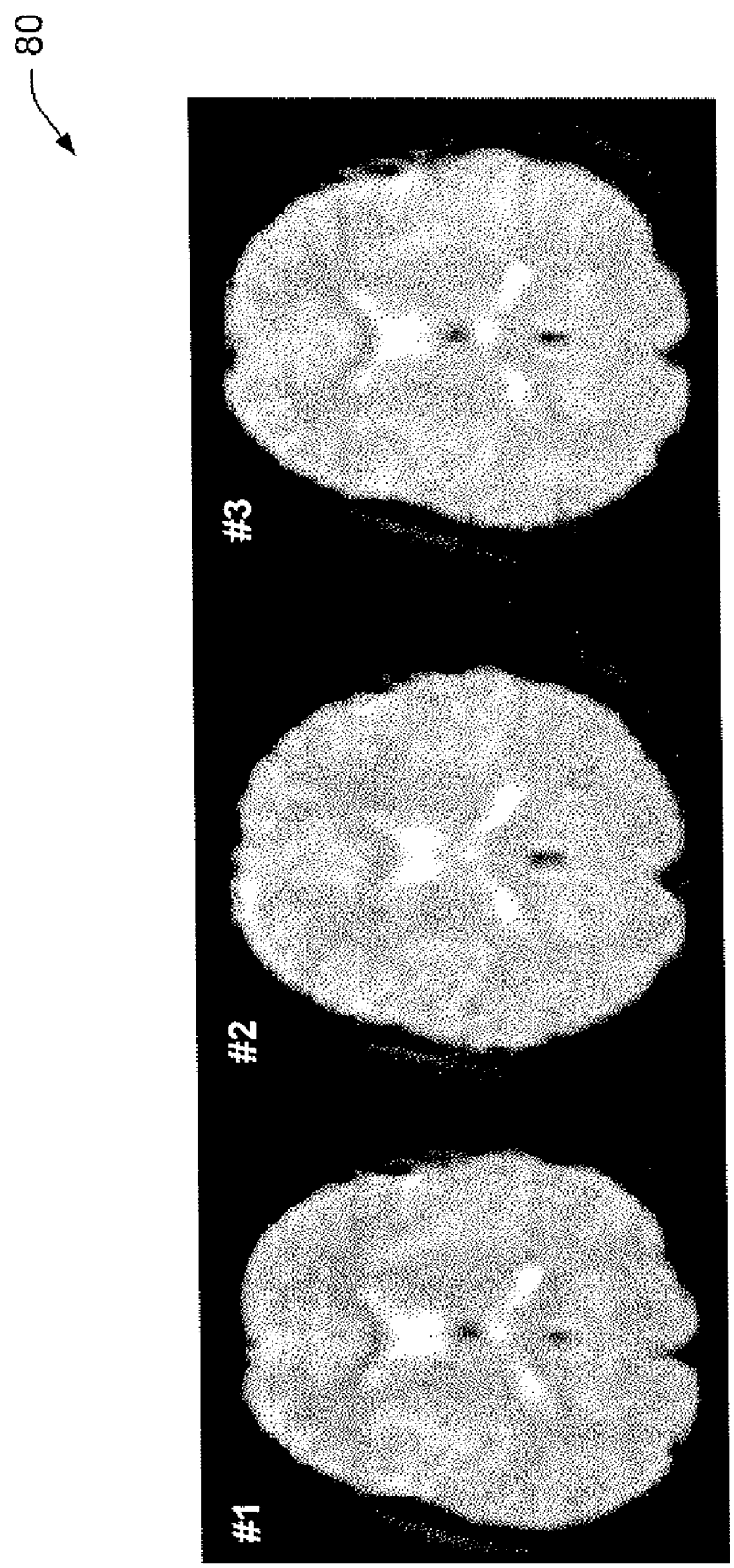
FIG. 2 shows an image in which three scan images (1, 2, and 3) are depicted, representing the position of a dynamic volume being scanned and corrected using PMC.

FIG. 2 shows an image 80 in which three scan images (1, 2, and 3) are depicted, representing the position of a dynamic volume being scanned and corrected using PMC. In the example presented in FIG. 2, the dynamic volume is a human brain, although other organs may be scanned and/or imaged in accordance with various embodiments. Subject motion during acquisition of a temporal image series results in volume-to-volume misalignment, which can corrupt data analysis such as functional magnetic resonance imaging (fMRI) activation mapping or the like. The described PMC algorithm(s) continually measure changes in geometry due to subject motion throughout a scan. Thus, PMC makes real-time adjustments to the ongoing scan so subsequent images are correctly aligned upon acquisition, thereby improving temporal volume alignment.

According to the example, images 1, 2, and 3 represent a dynamic image series with TR equal to three seconds. Following dynamic #1, the subject nods (e.g., approximately 9°), causing dynamic #2 to be misaligned. PMC algorithms detect the motion and make adjustments so the acquisition of dynamic #3 and subsequent dynamics are correctly aligned.

Figure 3:
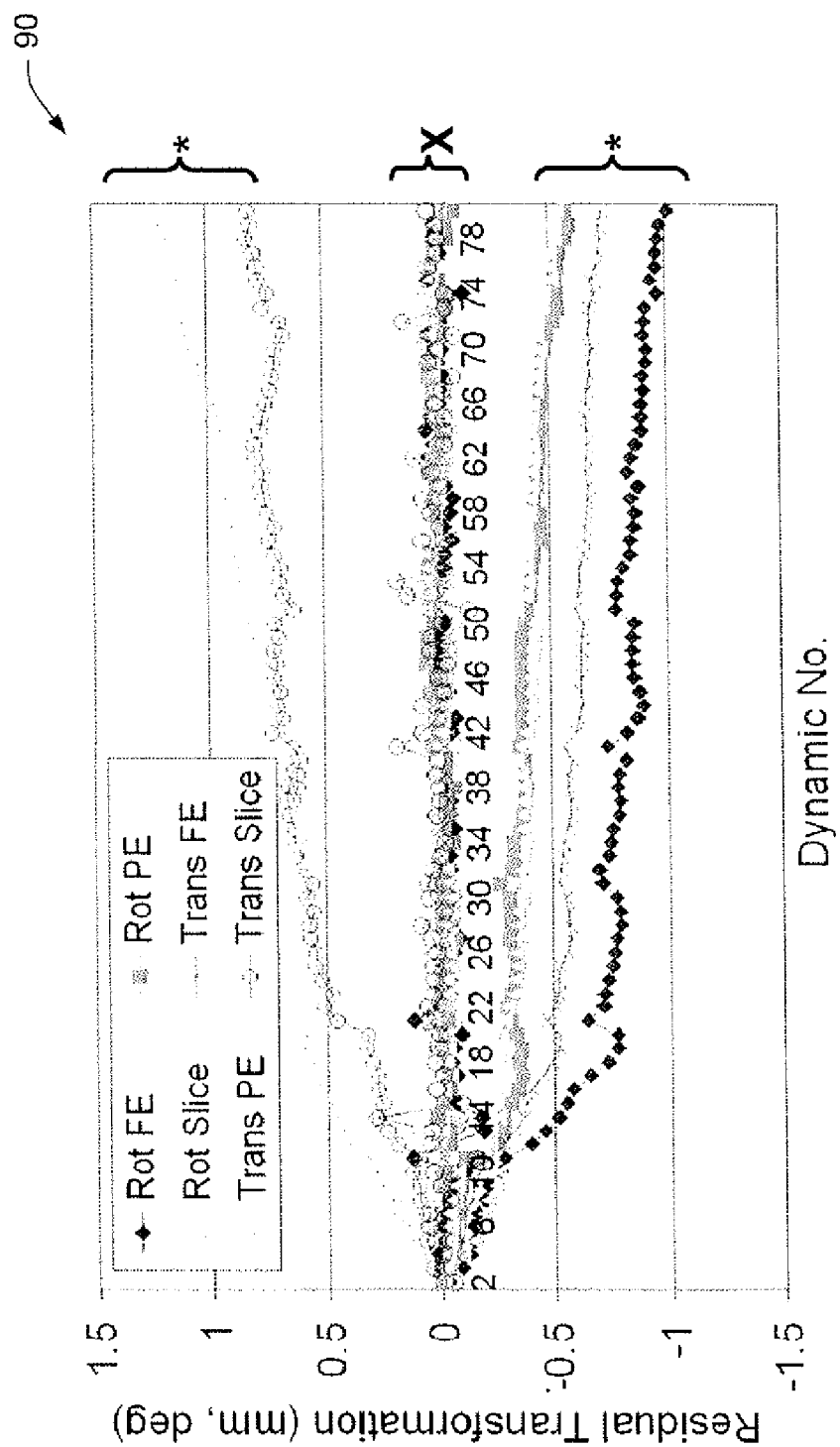
FIG. 3 is an illustration of a graphical comparison of prospective motion correction technique with a retrospective motion correction technique.

FIG. 3 is an illustration of a graphical comparison 90 of prospective motion correction technique with a retrospective motion correction technique. Retrospective motion correction, as part of post-processing, uses volume registration with pixel interpolation. Hence, retrospective correction is suitable for correcting in-plane transformations (e.g. x,y translations) that require simple shifts and rotations of image pixels, but unsuitable for correcting through-plane transformation (e.g. translation in the "slice" direction) that necessitate interpolation between slices, thereby introducing a significant partial-voluming effect. The image information lost during through-plane motion would be unable to be entirely recaptured by retrospective correction using interpolation. Thus, an advantage of PMC is that it can account for through-plane motions in real-time so that the image slices are reliably acquired at substantially their original locations and orientations, thereby mitigating a need for interpolation. In this manner, the acquired slices continuously maintain their alignment with the image volume series, minimizing any irrecoverable loss of image information.

The graphical comparison 90 of residual transformation data for dynamic studies acquired with retrospective motion correction (*) and PMC (X) is illustrated in FIG. 3. Transformation data for the retrospective motion correction dynamic series is calculated from the retrospective registration applied at each dynamic. The residual transformation data for the PMC dynamic series is calculated from post-processing registration performed on the PMC-corrected images. Rotations (in degrees) and translations (in millimeters) for frequency-encode (FE), phase-encode (PE), and slice axes are displayed on common axes.

The steady drift in rotation and translation in the retrospective data is attributed to involuntary subject motion (e.g., the relaxation of muscles, etc.) throughout the scan. The transformations using the retrospective approach require relatively large pixel transformations and interpolations for nearly every dynamic. Conversely, by continually correcting for subject motion throughout the dynamic series, the PMC images stay very close to the original geometry, and thus produce very minor residual transformations. In this manner, the PMC technique requires minimal pixel interpolation, while maintaining a high level of data integrity.

Figure 4:
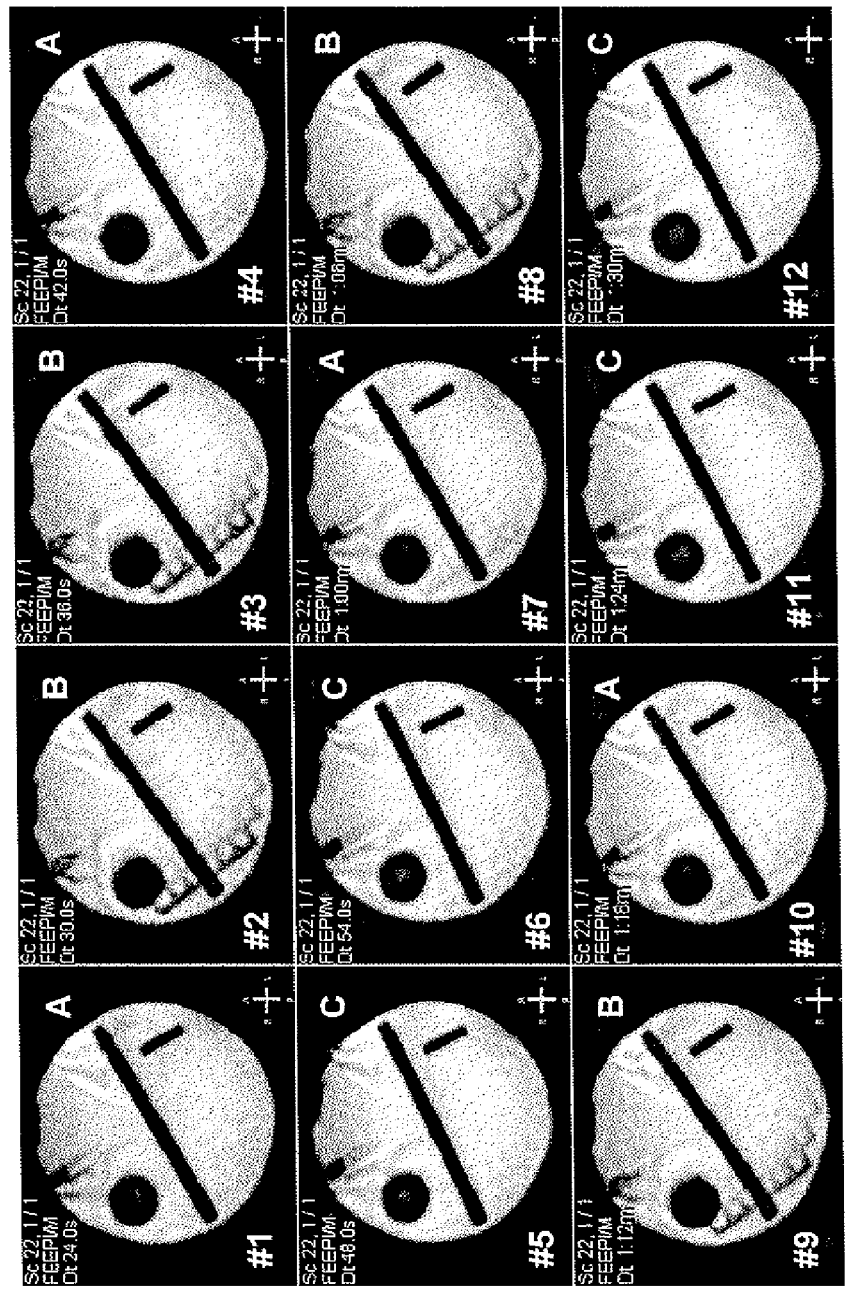
FIG. 4 illustrates an example of potential oscillatory pattern on a phantom dynamic series that undesirably arises using conventional prospective acquisition correction techniques.

FIG. 4 illustrates an example of potential oscillatory pattern on a phantom dynamic series 100 that undesirably arises using conventional prospective acquisition correction techniques. The dynamic number (1-12) is indicated on the lower left corner of each image and its corresponding geometry (A, B, C) is indicated on the upper right. The different geometry states can be discerned by the appearance of the grid and angle of the central bar in each phantom image. Dynamic #1 is in the original geometry state A. A motion occurs between dynamics #1 and #2 changing the geometry to state B. The motion is not corrected in time for #3 and hence #3 is also in state B. It is finally corrected in #4 back to state A. The duplicate transformation causes #5 to be over-corrected to geometry C, and this oscillation continues with the pattern A-B-B-A-C-C-, due to a single motion.

Using conventional systems and/or methods, the processes of image reconstruction, volume registration, geometry calculation, and data transfer require completion in the remaining time between the end of the acquisition of the last dynamic and the beginning of the next dynamic. In a system with a dedicated reconstructor and modern workstation, the total duration of these processes is on the order of seconds. For instance, it has been demonstrated using conventional prospective acquisition correction techniques, with scans with a 64×64 matrix and 16 slices and with a TR of 4 seconds, that the acquisition time is approximately 1.8 seconds, leaving approximately 2.2 seconds for completion of the correction process. Thus, in such conventional systems, TR is set to be sufficiently long to permit for completion of the requisite calculations. If TR is too short and the scanner does not receive geometry updates before the next acquisition is initiated, an undesirable oscillatory pattern arises.

Still referring to FIG. 4, consider the following course of events with a prospective acquisition correction technique for a scan with a short TR of 2 seconds (leaving only approximately 200 ms for calculations). A subject motion occurs following dynamic #1. Therefore dynamic #2 will be acquired with a different geometry than dynamic #1. A prospective acquisition correction technique can detect the difference between #1 and #2, and begins to work on calculating the necessary geometry updates (e.g., transformation 2→1). However, in the case of the short TR, the prospective acquisition correction technique cannot finish its calculations in time to provide the updates to the scanner before the acquisition of dynamic #3 is begun. Therefore, dynamic #3 will be acquired with the same "incorrect" geometry as dynamic #2. Dynamic #3 will therefore be skewed by the same transformation as dynamic #2. The prospective acquisition correction technique detects this different geometry as well and calculates a separate update for the scanner (transformation 3→1). Thus, if TR is too short when a prospective acquisition correction technique is utilized, a single motion can produce two updates: the legitimate initial update (2→1) and a duplicate (3→1). If nothing is done to halt the correction algorithm from sending both updates, the image series will fall into an oscillatory pattern. The legitimate transformation (2→1) will be applied in time for dynamic #4, and dynamic #4 will be caused to match the original geometry of dynamic #1. Additionally, the duplicate transformation (3→1) is still in the queue and will be applied for dynamic #5, causing dynamic #5 to be "over-corrected" beyond its original geometry, thus appearing as an artificially induced motion. The cycle will continue for this artificially induced motion, producing a continuous oscillation about the original position, all begun from a single movement.

In order to avoid this undesirable sequence of events, the minimum TR of a typical prospective acquisition correction technique acquisition is required to be of sufficient duration to leave the algorithm enough time for its calculations. This restriction limits TRs to relatively long values approximately 2 seconds longer than the minimum. The extended time can be even longer (e.g., approximately 2-4 seconds) if a larger image matrix or a larger number of slices is used. This limitation hinders MR applications in several ways. For example, it unnecessarily increases total scan time, restricts TR-related image contrast, limits temporal resolution of dynamic series, imposes conflicts with temporally correlated stimuli for fMRI, and introduces an oscillatory pattern if processing time extends beyond initial estimate due to unforeseen circumstances and/or performance on the workstation and reconstructor.

In contrast, the described PMC algorithm avoids TR-related limitations, allowing the user to freely adjust TR. PMC uses a data flow rate-independent model to apply geometry updates. Updates are delivered to the scanner on-the-fly, independent of the rate at which data is reconstructed and processed. Therefore, several dynamics can be safely acquired while the PMC algorithm calculates the original geometry transformation. Thus, PMC can be used for both long TR situations and short TR situations, which facilitates removing the timing related restrictions of conventional methods.

Figure 5:
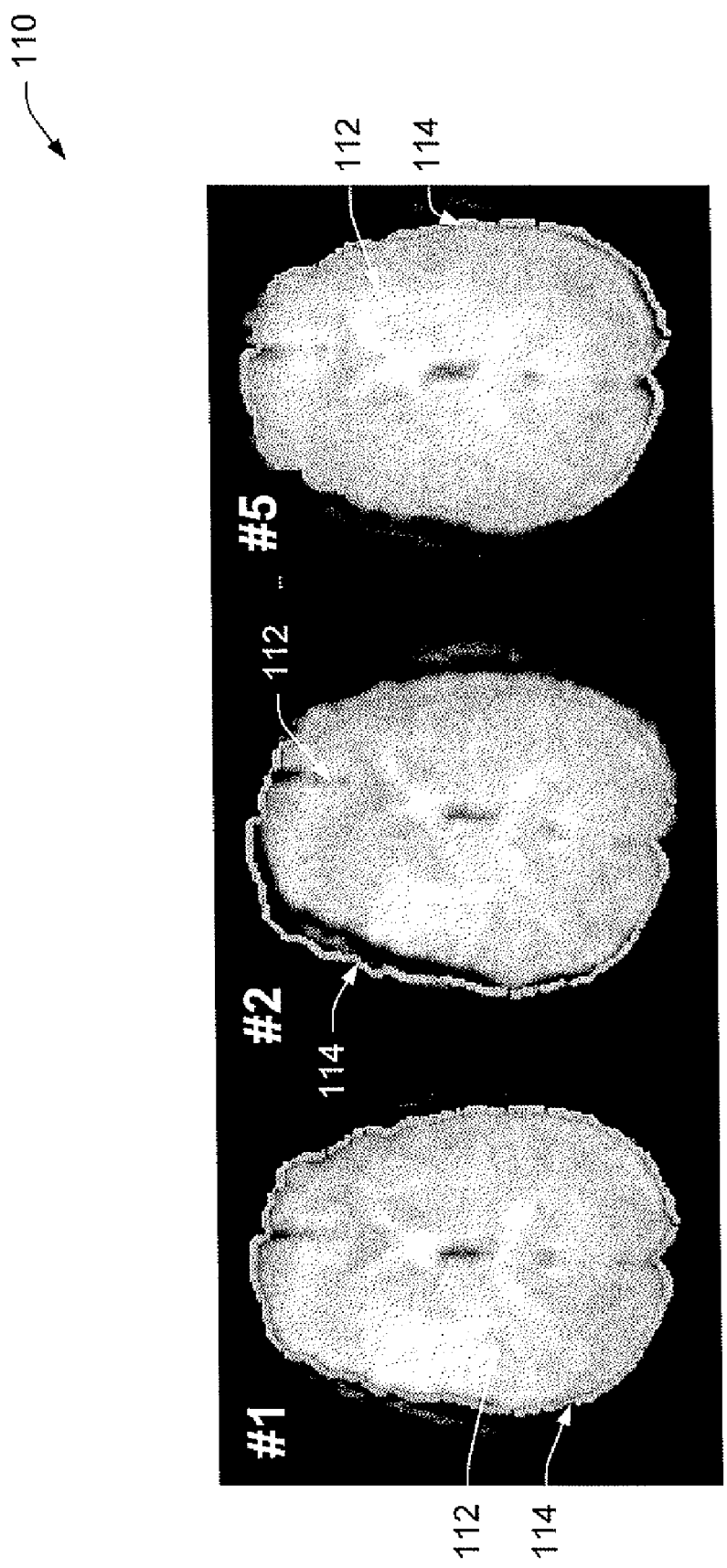
FIG. 5 illustrates a dynamic series acquired with short TR using a PMC technique.

FIG. 5 illustrates a dynamic series 110 acquired with short TR (e.g., approximately 1 second) using a PMC technique. The images (labeled 1, 2, and 5) in the series each show an actual orientation 112 and an expected orientation 114, of the dynamic volume being imaged (e.g., a patient's brain, in this example). Following dynamic 41, the subject's head tilts (e.g., approximately 5° according to this example), causing a misalignment between the actual and expected orientations of the patient's head. While the next scans are underway, the PMC algorithm detects the motion and sends the adjustments to the scanner, on the fly, in time for dynamic #5 to be correctly aligned.

An additional feature of PMC is "down-resolution" of images for registration processing, to save time and further mitigate TR-related complications. Incoming high-resolution images from reconstruction (e.g., 128×128, 256×256 and above) are re-interpolated into low-resolution images (e.g., 64×64 or less) before they are processed for registration. Since the duration of the registration process scales directly with matrix size, the total processing time is decreased, thereby increasing the probability that the geometry updates will be received by the scanner before the next scan is initiated. Moreover, the PMC algorithm includes a dynamically tunable registration algorithm. For instance, based on the data processing speed of the PMC component, the algorithm can self-adjust mid-way through a dynamic series to optimize the performance of the PMC algorithm.

Figure 6:
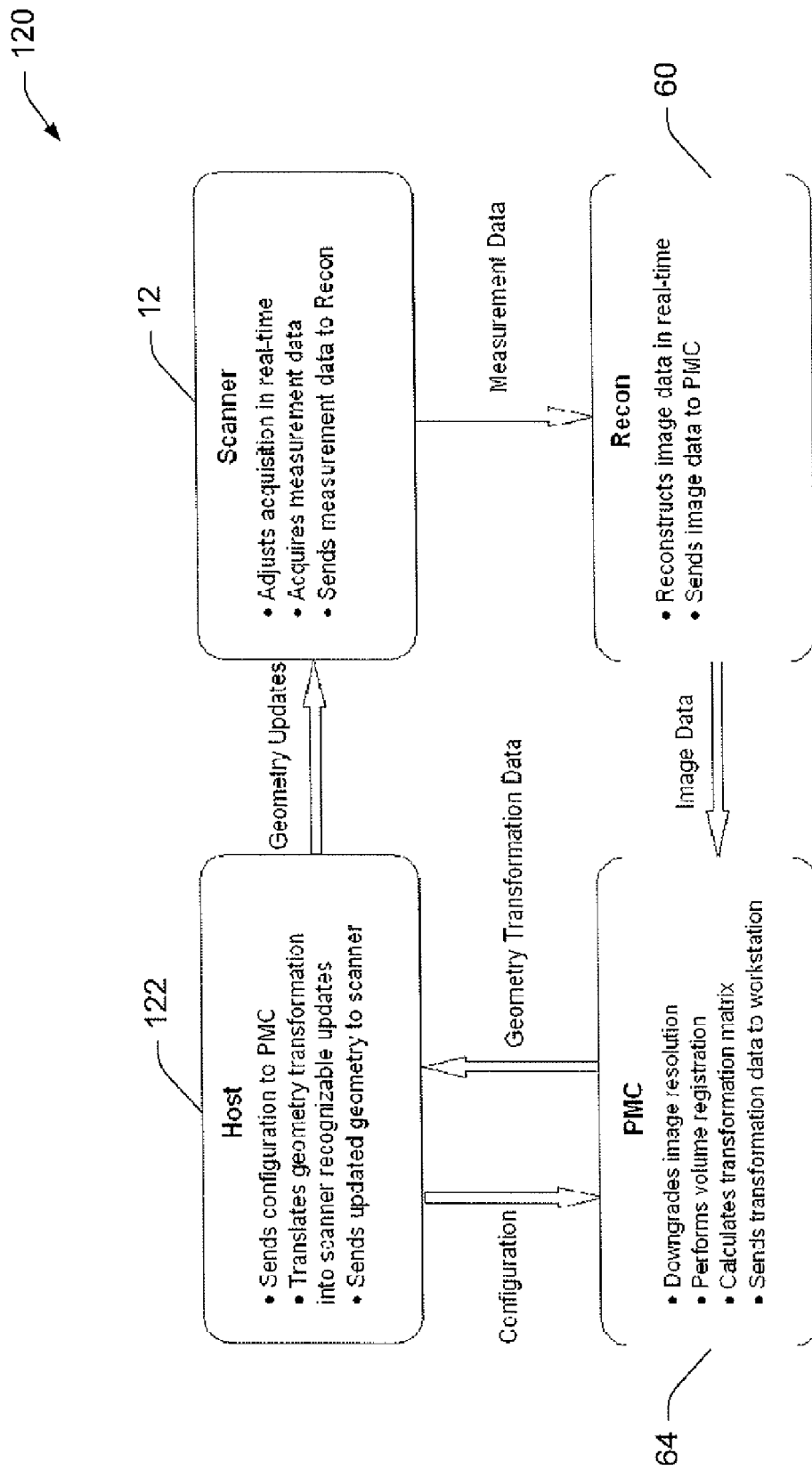
FIG. 6 illustrates a diagram of program flow for the PMC algorithm, in accordance with one or more embodiments.

FIG. 6 illustrates a diagram 120 of program flow for the PMC algorithm, in accordance with one or more embodiments. The diagram shows a host 122, which may be the user interface 38 of FIG. 1, a workstation operatively connected to a scanner and the PMC component, etc. The host provides geometry updates to the scanner 12, which in turn provides measurement data to the reconstruction processor 60. The reconstruction processor then provides image data to the PMC component 64, which provides geometry transformation data to the host. Additionally, the host provides configuration data to the PMC component. It is to be appreciated that the reconstruction processor 60 and the PMC component 64, as well as any associated databases (not shown) may be separate to from the host or may be integral thereto, in accordance with different embodiments. In some embodiments, the PMC 64 and reconstruction processor are implemented as software or firmware running on the host, such as a series of computer-executable routines for performing the various functions described herein.

The PMC program runs as a background application on a workstation, with connections to the scanner, reconstructor, and host program. The scanner acquires image volumes one dynamic at a time, and sends the measurement data to the reconstructor. The reconstructor reconstructs the images in real-time and sends the data to the PMC, which re-interpolates the incoming full-resolution images into low-resolution (e.g., 64×64 or less) image data to reduce registration time. Registration time scales to the data matrix size, and thus the processing time is decreased by working with down-resolution images rather than full-resolution images. The PMC calculates the geometry transformation of the current image volume with respect to a base volume (e.g., a first dynamic in a series) using a rigid-body registration algorithm. Upon completion of the registration of each dynamic volume, a six-parameter rigid-body transformation matrix is produced consisting of three rotations and three translations. The host program interprets the transformation data and converts it into a recognizable geometry that is sent to the scanner. The host program additionally keeps track of the geometry used to acquire each dynamic. The host program creates a package of updates for the scanner, which is retrieved by the scanner at its next opportunity. Subsequent dynamics are acquired on the scanner using the updated geometry, until a new transformation is encountered. In this manner, the program flow loops for the remainder of the scans in the dynamic series, and the scanner is updated on-the-fly to apply the corrections to the next dynamic as soon as they are ready.

Figure 7:
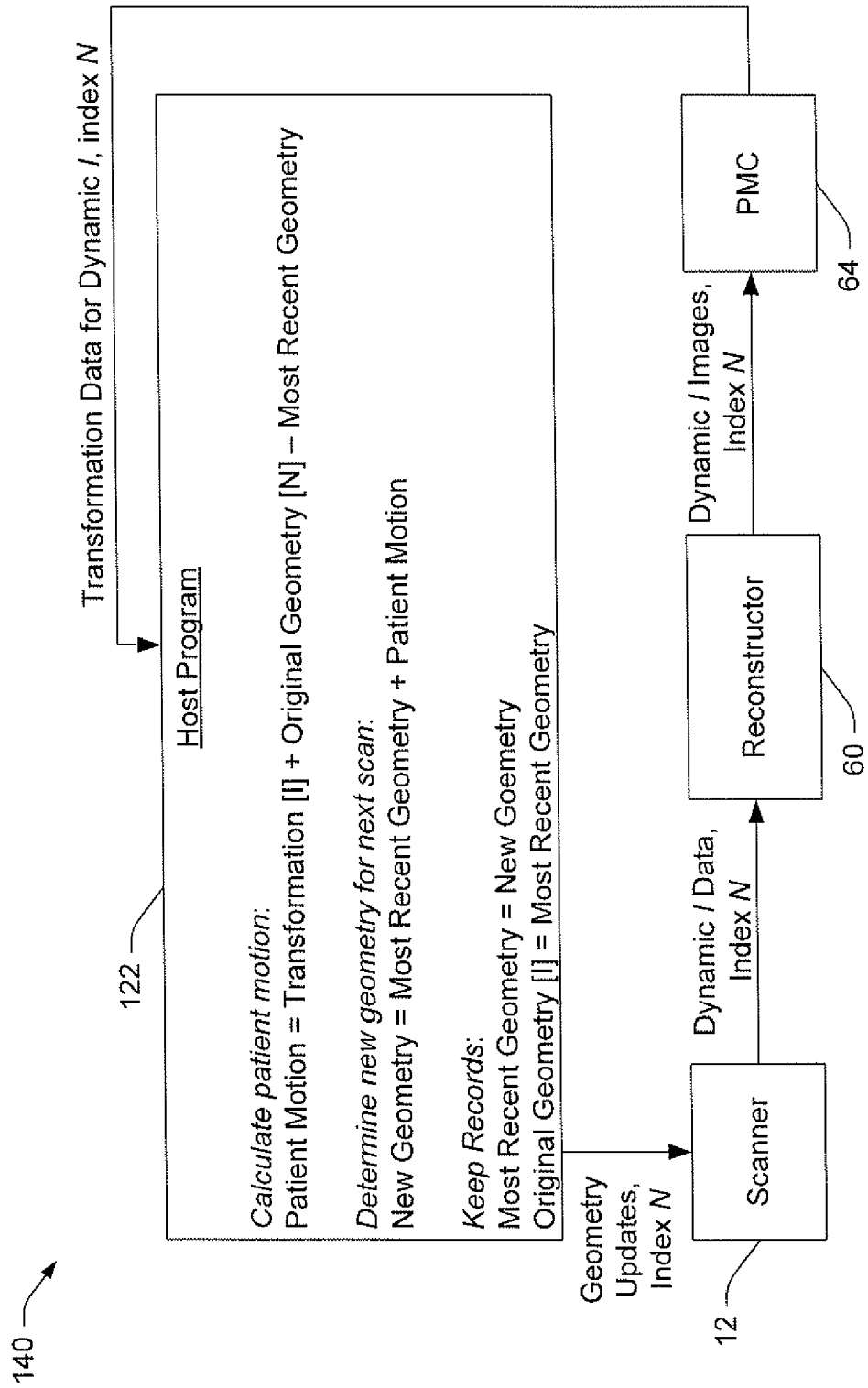
FIG. 7 illustrates a data flow rate-independent model for calculating geometry updates using a PMC algorithm.

FIG. 7 illustrates a data flow rate-independent model 140 for calculating geometry updates using a PMC algorithm. The process begins with the acquisition of dynamic data I (e.g., where I=N+n, where n=1, 2, . . . ) by the scanner 12, which is indexed and provided to the reconstruction processor 60. A feature of the process relates to record keeping of the geometry used to acquire each scan. Each incoming set of images from dynamic N causes the PMC component 64 to produce transformation data. The host program 122 accepts the transformation data from the PMC and generates a new geometry to be used for the acquisition of the next dynamic with index I. In the case where updates are available before the next scan, the index of the next dynamic that will use the new geometry information is determined as I=N+1. However, in the short TR situation where dynamics are skipped, I=N+n, where n>1.

The new geometry is kept in a record (e.g., a database or memory) by the host program along with the index of the image whose transformation data was used to generate the new geometry (N). The geometry updates and index are sent to the scanner to be picked up on the fly for the next available scan. Once the updates are obtained by the scanner, the scanner tags the forthcoming measurement data for dynamic I with an auxiliary data tag which carries the index N. In this manner, the current image set carries a record of the geometry that was used to create it. The reconstructor attaches the index N to each image from dynamic I that it outputs to the PMC. The PMC calculates the transformation data for dynamic I and passes along the index N to the host program. The host program calculates the new geometry based on the most recent geometry and the incoming transformation data. Using the index N, the host program evaluates its record to determine the original geometry used to acquire the current image set. The host program compares the most recent geometry with the new geometry derived from the transformation data for dynamic I, and the difference between the two geometries is determined to be the actual patient motion. The patient motion is then added to the current geometry to create the new geometry. The new geometry is sent to the scanner and a record of the current geometry and original geometry is maintained. In this manner, the data flow iteratively continues, and geometry updates are applied by the scanner on-the-fly as they are ready. The next dynamic (e.g., with index >=I+n) can be updated using the geometry information derived from image I, and can carry the index I.

According to an example, if updates cannot reach the scanner in time for the next acquisition (n>1), multiple dynamics will be acquired with the same geometry. Each dynamic carries the same index N, which references the geometry with which it was acquired. When those dynamics (with I=N+1, N+2, etc.) are processed by the PMC, they produce substantially identical transformation data. In conventionally systems, each of these transformations would be applied leading to the oscillatory state. However, the PMC maintains the record of the original geometry, and thus only the first transformation registers patient motion, resulting in a change to the most recent geometry. Since the subsequent transformations produce substantially the same transformation data, they will produce the same new geometry because they were acquired with the same original geometry. Accordingly, calculations using the latter transformation data will generate zero patient motion, thus protecting the algorithm from entering an oscillatory pattern.

Figure 8:
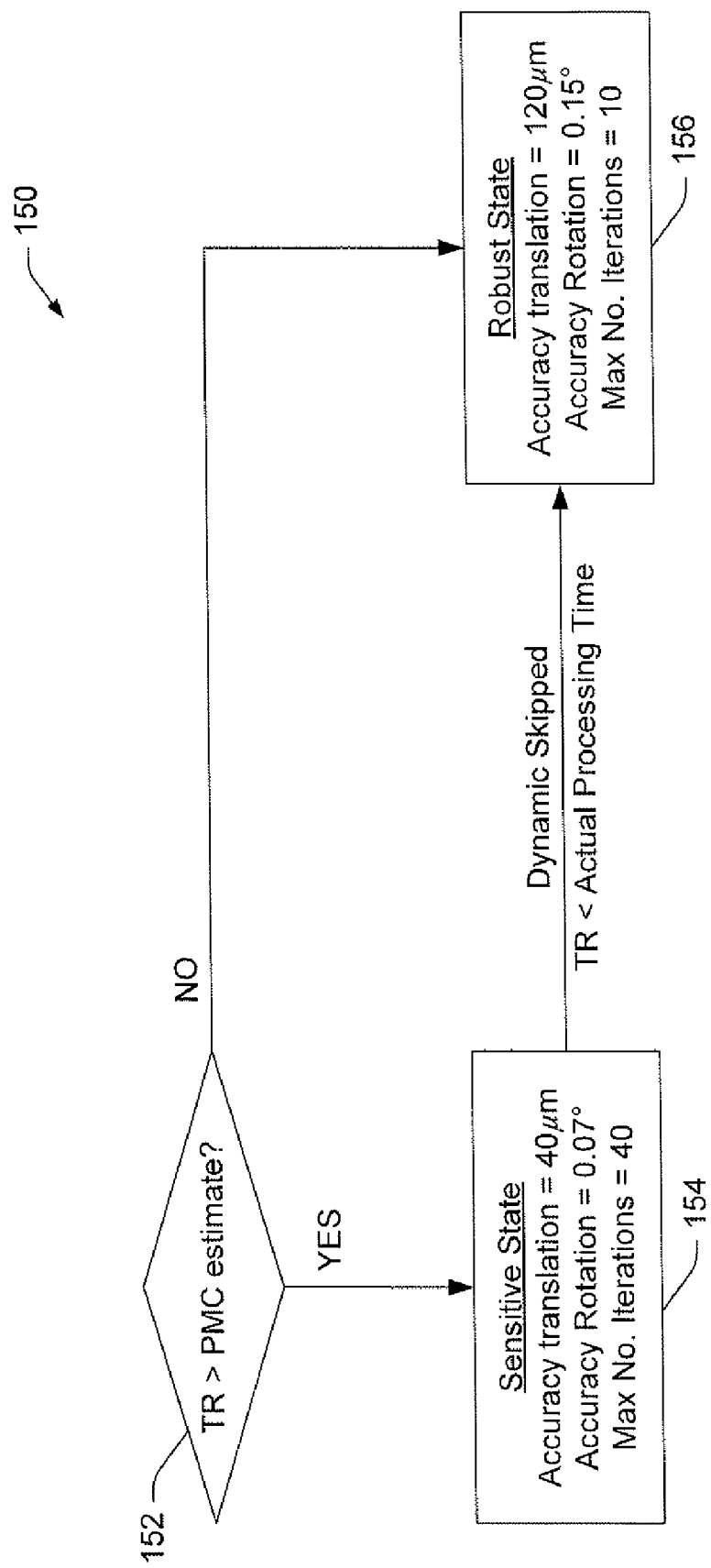
FIG. 8 illustrates a decision algorithm for setting a PMC registration algorithm state.

FIG. 8 illustrates a decision algorithm 150 for setting a PMC registration algorithm state. The algorithm includes determining whether TR is greater than an estimated PMC processing time, at 152. If TR is greater than the estimated processing time for the PMC, then at 154, the PMC is set to a sensitive registration algorithm state. In this state, for example, various parameters associated with accuracy of translation and/or rotation, maximum number of iterations, etc., may be set to predetermined values or ranges. According to the depicted example, translation accuracy is set to approximately 40 micrometers, rotation accuracy is set to approximately 0.07 degrees, and a maximum of approximately 40 iterations are permitted.

If TR is less than actual PMC processing time, then one or more dynamics may be skipped, and the PMC is set to a robust registration algorithm state, at 156, where more robust parameter values are employed. For instance, according to an example, the robust state parameter values may include setting the translation accuracy to approximately 120 micrometers, the rotation accuracy to approximately 0.15 degrees, and permitting a maximum of approximately 10 iterations. Additionally or alternatively, the PMC can be set directly to the robust registration state upon a determination that the TR is not greater than the estimated PMC processing time. It will be appreciated that the foregoing examples of parameter values are described for illustrative purposes to show relationships between sensitive and robust states and/or values, and that the subject innovation is not limited to such values.

The registration algorithm in the PMC can thus be adjusted with regard to the desired accuracy level and maximum number of iterations. Registrations with high accuracy and a large number of iterations are more sensitive to small motions, at the expense of longer processing times. Registrations with low accuracy and few iterations are relatively insensitive to fine motions, but generally robust for larger motions and much faster. For this reason, PMC can be run in one of the two states described above: sensitive and robust. The sensitive state permits fine adjustments to be made to compensate for small involuntary motions, such as in fMRI studies. The robust state facilitates addressing situations where bulk motion is expected to be large and/or where speed/TR is important. The values of registration parameters are specified, as part of the configuration of PMC, by the host program performed at the beginning of every scan. The parameter values are adjusted as a group for each state and can be modified by the user via system-level parameters.

The selection of the state is a function of an estimation of the total required processing time (e.g., for reconstruction, registration, calculation, and data transfer). Based on the estimation, if it appears that TR is sufficiently long that the PMC algorithm can produce its updates safely before the next scan is initiated, the algorithm is tuned in the sensitive state. If TR is not expected to be long enough, the algorithm is tuned to offer more robust data in a quicker turnaround time.

The PMC algorithm also includes a "safety valve" to further optimize performance. For instance, if a dynamic is skipped because TR is not long enough for the actual processing time, while in the sensitive state due to an unforeseen extension of processing/reconstruction time, the algorithm can dynamically adjust its configuration on-the-fly to the robust state for the duration of the scan.

Figure 9:
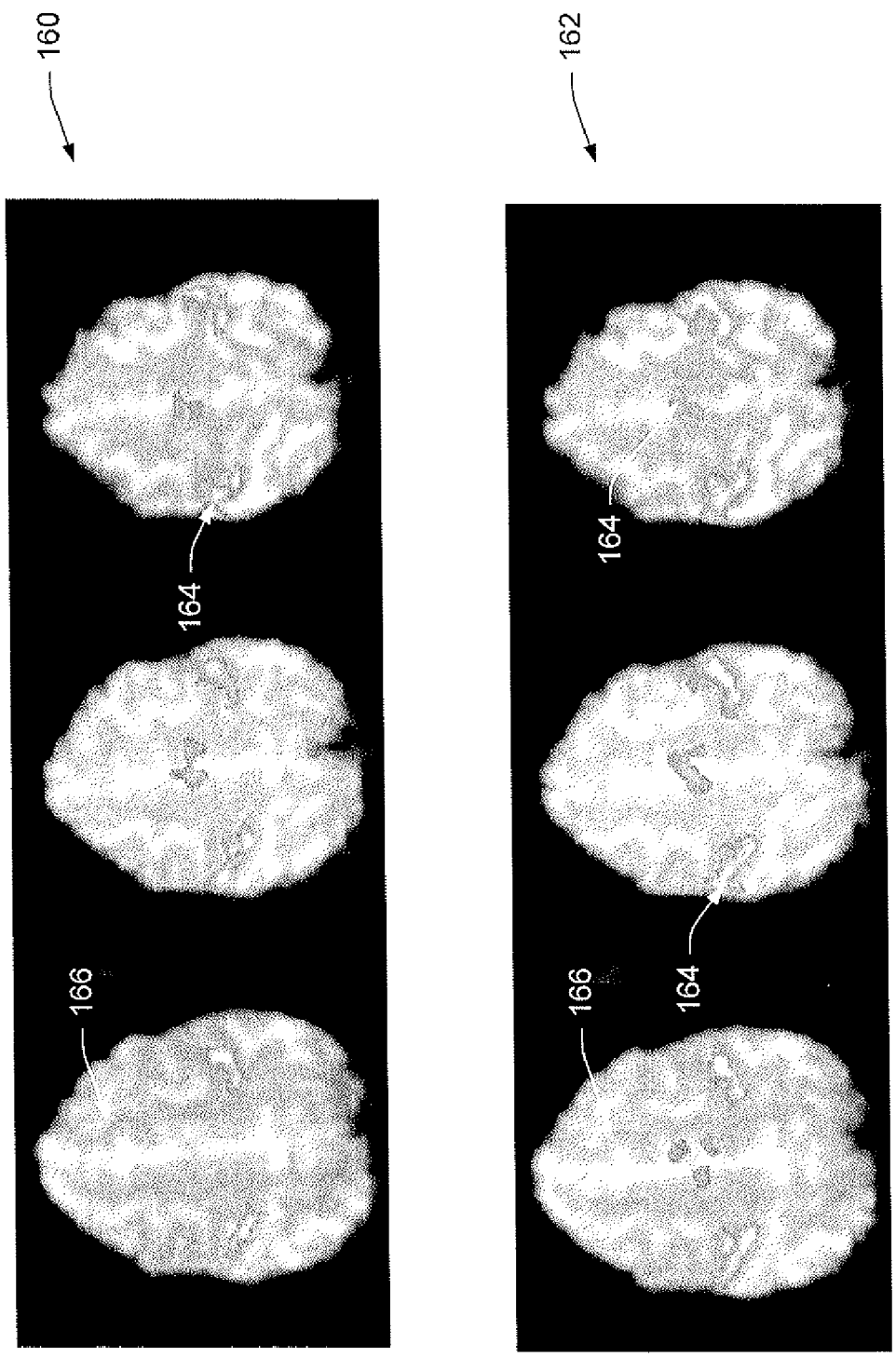
FIG. 9 illustrates a comparison of three contiguous "slices" from cross-correlation activation maps calculated without PMC and with PMC.

FIG. 9 illustrates a comparison of three contiguous "slices" from cross-correlation activation maps calculated without PMC 160 and with PMC 162. The regions of activation 164 in the PMC-enabled maps are generally brighter and more congruous with the gray matter 166 anatomy. As illustrated active regions 164 in the maps calculated with PMC 162 are both more numerous and more robust.

PMC is applicable for dynamic scanning applications for which image volume alignment is important. PMC has particularly important applications for neurological MR, specifically fMRI. By producing superior image volume alignment compared to retrospective motion correction, fMRI activation maps are improved with respect to the specificity and statistical significance of the activation areas. By removing the TR-related limitations, the described PMC systems and methods offer a strategic advantage over conventional techniques. Additionally, PMC can be used with a wider variety of fMRI paradigms, temporal resolutions, and acquisition matrices.

Figure 10:
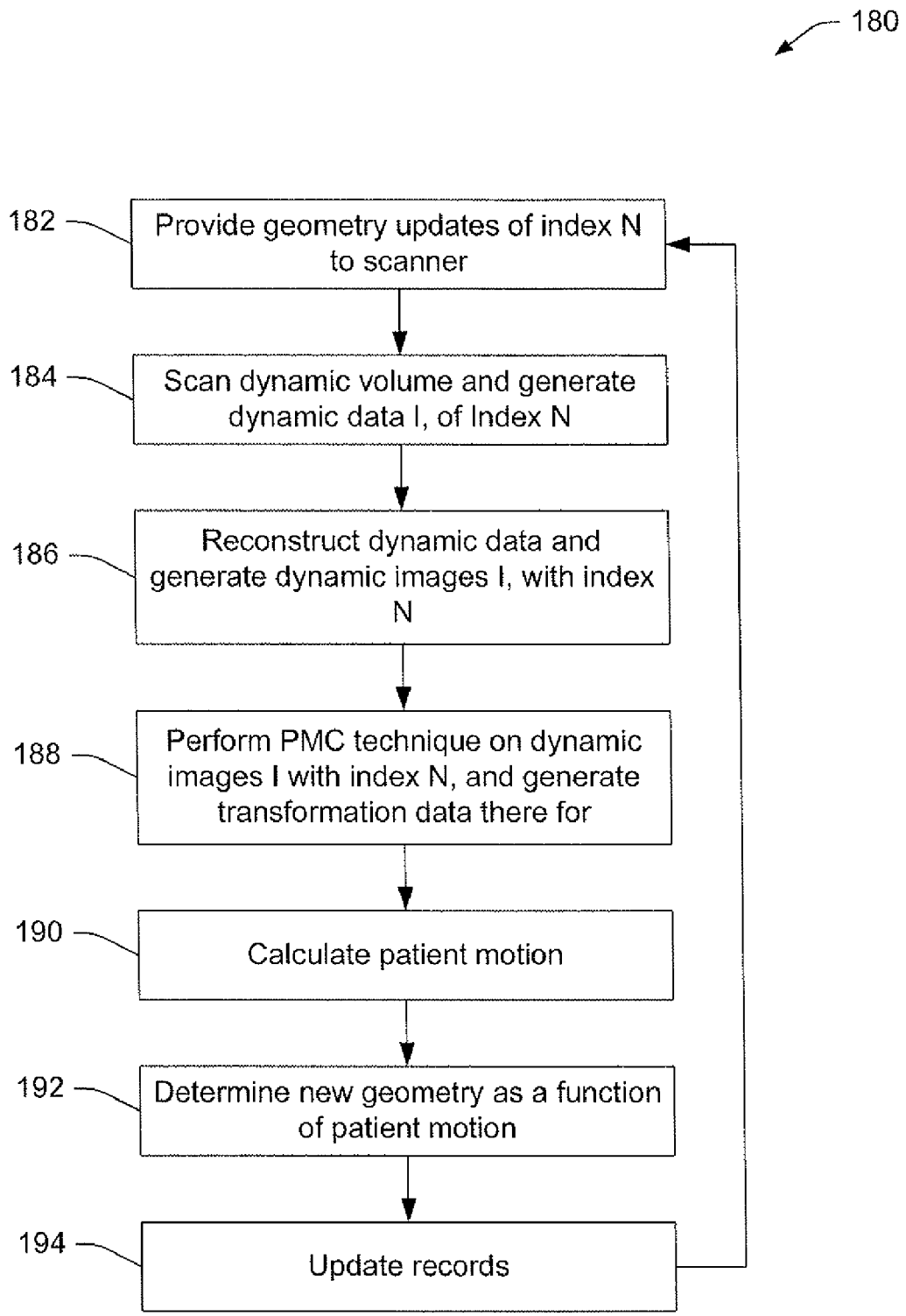
FIG. 10 illustrates a method for performing a PMC technique, in accordance with one or more aspects presented herein.

FIG. 10 illustrates a method 180 for performing a prospective motion correction (PMC) technique, in accordance with one or more aspects presented herein. At 182, geometry updates having an index of N are provided to a scanner, such as a magnetic resonance imaging machine. If a scanning procedure is at its inception, then the "updates" comprise an initial geometry for the dynamic volume (e.g., organ or other patient tissue) to be scanned. The index N describes an original geometry used to acquire a dynamic image or set of images, in a first iteration of the method, and dynamic image data I is generated during a scan of the dynamic volume, at 184. At 186, dynamic data I is reconstructed to generate the images. At 188, a PMC protocol is executed on the dynamic images I with the index N, and transformation data is generated there for. That is, each incoming set of images from dynamic N causes the PMC algorithm to produce transformation data. The transformation data describes a change in position of the dynamic volume from an expected position based on the original geometry, N.

Patient (or volume) motion is calculated at 190 based on PMC information and transformation data. For instance, patient motion is determined as the sum of the transformation [I] and the original geometry [N] less the most recent geometry. According to one embodiment, a host program receives the transformation data from the PMC algorithm and generates a new geometry to be used for the acquisition of the next dynamic with index I. In the case where updates are available before the next scan, the index of the next dynamic that will use the new geometry information is determined as I=N+1. However, in the short TR situation where dynamics are skipped, I=N+n, where n>1. During the first iteration, the most recent geometry is the original geometry, so the patient movement is equal to the change in position represented by the transformation data [I]. At 192, a new geometry for a subsequent scan period is determined, as a function of the calculated patient motion. For instance, if the patient's brain is the dynamic volume being scanned, and the patient's head rotates 5 degrees between dynamic image collection periods in a 30-minute scan, then the new geometry is rotated to match the rotation of the patient's head to ensure that subsequent dynamics (image scans) have the same alignment as scans prior to the rotation of the head. Thus, the new geometry is calculated as the sum of the most recent geometry and the patient movement.

At 194, data records are updated to reflect the changes in patient position. For instance, the new geometry calculated at 192 is recorded as the most recent geometry, and is sent to the scanner to be added as an index for a next set of dynamic image data. In this manner, records are kept of the geometry used to acquire each scan of the dynamic volume. That is, each new geometry is kept in a record (e.g., a database or memory) along with the index of the image whose transformation data was used to generate the new geometry (N). Geometry updates and indices are sent to the scanner to be picked up on the fly for the next available scan. Once the updates are obtained by the scanner, the scanner tags the forthcoming measurement data for dynamic I with an auxiliary data tag which carries the index N. In this manner, the current image set carries a record of the geometry that was used to create it. The index N is attached to each image from dynamic I that it outputs to the PMC algorithm.

According to one embodiment, the method reverts to 182 for another iteration wherein the PMC algorithm calculates the transformation data for dynamic I and passes along the index N to the host program. The host program calculates the new geometry based on the most recent geometry and the incoming transformation data. Using the index N, the host program evaluates its record to determine the original geometry used to acquire the current image set. For instance, the host program compares the most recent geometry with the new geometry derived from the transformation data for dynamic I, and the difference between the two geometries is determined to be the actual patient motion. The patient motion is then added to the current geometry to create another new geometry. The new geometry is again sent to the scanner and a record of the current geometry and original geometry is maintained. In this manner, the data flow iteratively continues, and geometry updates are applied by the scanner on-the-fly as they are ready. The next dynamic (e.g., with index greater than or equal to I+n) can be updated using the geometry information derived from image I, and can carry the index I.

Having thus described the preferred embodiments, the invention is now claimed to be:

1. A system for prospective motion correction (PMC), including:
    a scanner that scans a dynamic volume in a patient;
    a reconstructor that reconstructs measurement data received from the scanner into image data;
    a PMC component that analyzes the image data and generates geometry transformation data related to a change between a most recent geometry associated with an orientation and position of the dynamic volume and a new geometry associated with the orientation and position of the dynamic volume; and
    a host that generates geometry updates for the scanner between successive scans as a function of the geometry transformation data;
    wherein the PMC component downgrades image resolution, performs a volume registration protocol, calculates a transformation matrix, and provides the transformation data to the host.

2. The system according to claim 1, wherein the host translates the geometry transformation data into scanner-readable geometry update information and provides the geometry update information to a scan controller that controls the scanner.

3. The system according to claim 2, wherein the scan controller adjusts a scanning geometry for a subsequent scan of the dynamic volume according to the geometry update information.

4. The system according to claim 1, wherein the host provides configuration information to the PMC component, the configuration information including an original geometry used by the scanner during a first scan.

5. The system according to claim 1, wherein the host calculates patient motion as a function of the geometry transformation information, the original geometry, and a most recent geometry of the dynamic volume.

6. The system according to claim 5, wherein the host calculates patient motion as the sum of a geometry transformation value (I) and the original geometry (N), minus the most recent geometry of the dynamic volume.

7. The system according to claim 5, wherein the host calculates a new geometry as the sum of the most recent geometry of the dynamic volume and the calculated patient motion.

8. The system according to claim 1, wherein the host stores a record of geometries associated with respective scans, and indexes image data according to the geometry employed during the scan from which the image data was acquired.

9. The scanner according to claim 1, wherein the scanner is a magnetic resonance imaging (MRI) machine.

10. The system according to claim 1, wherein the host includes:
    a routine or means for providing geometry updates to the scanner;
    a routine or means for scanning the dynamic volume;
    a routine or means for reconstructing measurement data of the dynamic volume into image data;
    a routine or means for generating transformation data that describes a change in position of the dynamic volume;
    a routine or means for calculating patient motion as a function of the transformation data;
    a routine or means for calculating a geometry update as a function of the calculated patient motion; and
    a routine or means for storing information related to successive geometries and image data acquired using respective geometries.

11. A method for performing the prospective motion correction in the system of claim 1, including:
    providing an initial geometry to a scanner;
    scanning the dynamic volume;
    generating measurement data indexed to the initial geometry;
    reconstructing the measurement data and generating image data indexed to the initial geometry;
    executing a PMC protocol to calculate transformation information from the image data;
    calculating patient motion as a function of the transformation information and the initial geometry;
    determining a new geometry as a function of the patient motion;
    providing the new geometry to the scanner for a subsequent scan; and
    repeating the scanning, generating, reconstructing, executing, calculating, determining and providing steps using the new geometry.

12. A method of performing prospective motion correction during a patient scan, including:
    providing an original geometry to a scanner;
    scanning the dynamic volume;

generating image data indexed to an original geometry;

executing a PMC protocol that calculates transformation information from the image data, the PMC protocol comprising downgrading image resolution, performing a volume registration protocol, calculating a transformation matrix, and providing the transformation data to a host;

calculating patient motion as a function of the transformation information and the original geometry;

determining a new geometry as a function of the patient motion;

providing the new geometry to the scanner for a subsequent scan; and repeating the scanning, generating, executing, calculating, determining and providing steps using the new geometry.

13. The method according to claim 12, further including estimating PMC processing time and comparing the estimated time to a repetition time (TR) for the scan.

14. The method according to claim 13, further including setting the PMC protocol to a sensitive registration state if the estimated PMC processing time is less than or equal to the TR.

15. The method according to claim 14, further including dynamically changing the registration state of the PMC protocol upon a determination that the TR is less than an actual PMC processing time.

16. The method according to claim 13, further including setting the PMC protocol to a robust registration state if the estimated PMC processing time is greater than the TR.

17. The method according to claim 12, further including calculating the patient motion as a function of the transformation data and the difference between the original geometry and a most recent geometry.

18. The method according to claim 17, wherein the transformation data describes a difference between current position of the dynamic volume and a position of the dynamic volume during a most recent previous scan.

19. The method according to claim 12, wherein the scanner is a magnetic resonance imaging (MRI) machine.

20. A processor or computer-readable medium programmed to perform the method of claim 12.

21. A prospective motion correction system, including:
means for providing an initial geometry to a means for scanning a dynamic volume;
means for scanning the dynamic volume and generating measurement data indexed to an initial geometry;
means for reconstructing the measurement data and generating image data indexed to the initial geometry;
means for executing a PMC protocol to calculate position change data from the image data, wherein the means for executing the PMC protocol downgrades image resolution, performs a volume registration protocol, calculates a transformation matrix, and provides the transformation data to the host;
means for calculating patient movement as a function of the position change data and the initial geometry;
means for determining a new geometry as a function of the patient movement;
means for providing the new geometry to the means for scanning for a subsequent scan; and
means for repeating the scanning, reconstructing, executing, calculating, determining and providing steps using the new geometry.

22. The system according to claim 21, further including bookkeeping means that prevents oscillatory motion correction.

* * * * *